(12) United States Patent
Coyle (10) Patent No.: US 11,389,636 B2
(45) Date of Patent: Jul. 19, 2022

(54) CONNECTOR CAP WITH SAFETY VENT (71) Applicant: Becton, Dickinson and Company, Franklin Lakes, NJ (US)

(72) Inventor: Sean James Coyle, Tenafly, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 380 days.

(21) Appl. No.: 16/014,156

(22) Filed: Jun. 21, 2018

(65) Prior Publication Data
US 2018/0369561 A1    Dec. 27, 2018

Related U.S. Application Data (60) Provisional application No. 62/523,506, filed on Jun. 22, 2017.

(51) Int. Cl.
*A61M 39/20* (2006.01)
*A61M 39/16* (2006.01)

(52) U.S. Cl.
CPC ............ *A61M 39/20* (2013.01); *A61M 39/16* (2013.01); *A61M 2039/205* (2013.01)

(58) Field of Classification Search
CPC .................. A61M 39/20; A61M 2039/205
See application file for complete search history.

(56) References Cited

U.S. PATENT DOCUMENTS

| 3,843,006 | A |  | 10/1974 | Naito et al. |
| 5,876,475 | A |  | 2/1999 | Volpe |
| 5,954,957 | A |  | 9/1999 | Chin-Loy et al. |
| 6,491,667 | B1 | * | 12/2002 | Keane ................. A61B 5/15003 604/181 |
| 8,740,864 | B2 |  | 6/2014 | Hoang et al. |
| 10,391,265 | B2 |  | 8/2019 | Lazarof |
| 2002/0027120 | A1 |  | 3/2002 | Miceli et al. |
| 2004/0074859 | A1 | * | 4/2004 | Hanna .................... A61J 11/008 215/11.1 |
| 2005/0165351 | A1 |  | 7/2005 | Tamagni |
| 2009/0028750 | A1 |  | 1/2009 | Ryan |
| 2009/0223963 | A1 | * | 9/2009 | Bisio .................. B65D 41/3433 220/304 |
| 2011/0224651 | A1 | * | 9/2011 | Ziman ................... A61M 39/10 604/533 |
| 2011/0314619 | A1 |  | 12/2011 | Schweikert |
| 2012/0111368 | A1 |  | 5/2012 | Rahimy et al. |
| 2012/0216359 | A1 |  | 8/2012 | Rogers et al. |

(Continued)

FOREIGN PATENT DOCUMENTS

| CN | 102627165 A | 8/2012 |
| CN | 105339037 A | 2/2016 |

(Continued)

*Primary Examiner* — Jenna Zhang
(74) *Attorney, Agent, or Firm* — Dickinson Wright PLLC (57) ABSTRACT

A needleless connector caps is provided with one or more vents allowing air to pass around the cap, for example in a case where a cap may be accidentally lodged in a position completely concentric with a patient's throat. Configuration of structural elements making up a cap exterior can provide one or more openings or channels in the cap that remain unblocked and extend from the base to the top side of the cap forming one or more vents allowing air to pass through the cap.

11 Claims, 7 Drawing Sheets

(56) References Cited

U.S. PATENT DOCUMENTS

2013/0270270 A1* 10/2013 Reinders ............ B65D 75/5883
                                                                220/276
2014/0188089 A1    7/2014 Midgette et al.
2016/0325089 A1   11/2016 Burkholz
2017/0203092 A1    7/2017 Ryan et al.
2018/0304067 A1   10/2018 Ryan

FOREIGN PATENT DOCUMENTS

| DE | 29609596 U1 | 10/1996 |
| WO | WO-2008100950 A2 | 8/2008 |
| WO | WO-2010141508 A1 | 12/2010 |
| WO | WO-2011066586 A1 | 6/2011 |
| WO | 2013149500 A1 | 10/2013 |

* cited by examiner

CONVENTIONAL
FIG.1

CONVENTIONAL
FIG.2

CONNECTOR CAP WITH SAFETY VENT

CROSS-REFERENCE TO RELATED APPLICATIONS

This application claim priority under 35 USC § 119(e) from U.S. Provisional Patent Application No. 62/523,506 filed on Jun. 22, 2017, the contents of which (including all attachments filed therewith) are hereby incorporated by reference in their entirety.

TECHNICAL FIELD

Generally, exemplary embodiments of the present invention relate to the fields of medical caps, including medical disinfection caps, and in particular caps and/or disinfection caps for uses with IV needleless connectors.

BACKGROUND

Figure 1:
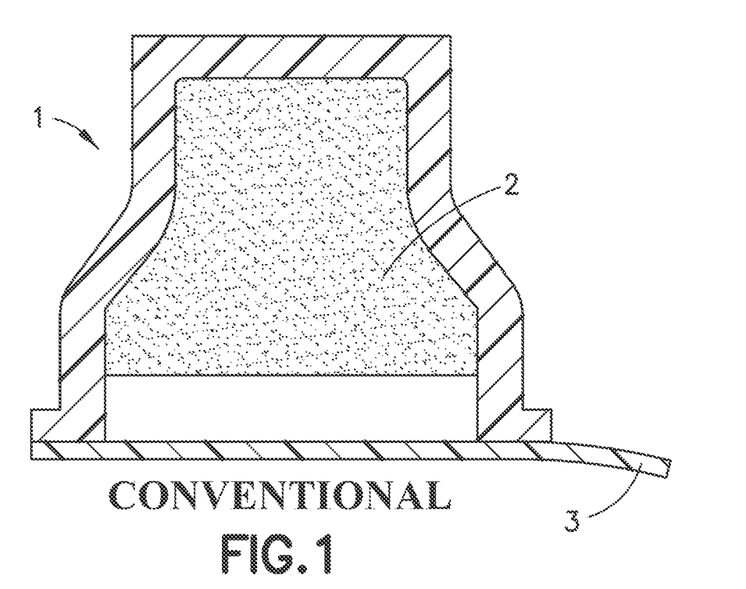
FIGS. 1 and 2 are cross sectional views of conventional caps for needleless connectors.
Figure 2:
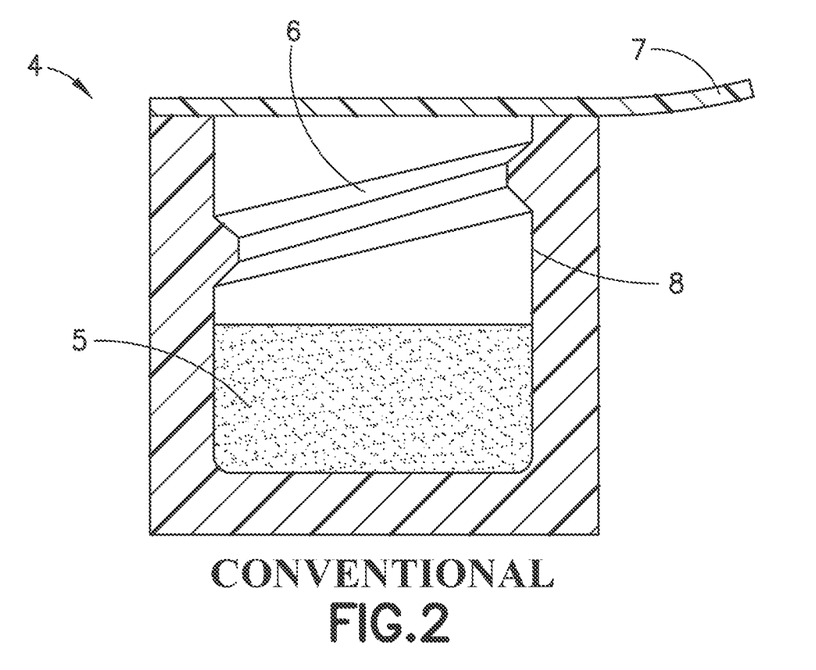

In developed markets, when utilizing an IV catheter, a needleless connector will typically be used to close off the system and then subsequently accessed to administer medication or other necessary fluids via the catheter to the patient. Various conventional caps for closing off a needleless connector while not in use have been known for some time. In order to decrease Catheter-related bloodstream infection (CRIBS) cases disinfection caps were originally disclosed in U.S. Patent Publication No. 2007/0112333 which issued as U.S. Pat. No. 8,740,864 (the entire disclosures of both of which are incorporated herein by reference), and introduced on the market. Disinfection caps such as those disclosed in the U.S. Pat. No. 8,740,864 are illustrated in FIGS. 1 and 2 herein, where cap 1 includes a disinfecting pad 2 and a lid 3, and cap 4 includes a disinfecting pad 5 and lid 7, as well as threads 6 on its inner circumference 8 to interlock with needleless connector hub. On the other hand, other convention caps may have similar features but exclude the disinfecting pad. Disinfection caps have been added to the Society for Healthcare Epidemiology of America (SHEAF) guidelines and early indications are that caps will also be incorporated into the 2016 Infusion Nurses Standards (INS) guidelines.

Further improved designs for disinfection caps are disclosed in related U.S. patent application Ser. No. 15/408,278 (issued as U.S. Pat. No. 10,391,265 on Aug. 27, 2019) and U.S. patent application Ser. No. 15/408,187 (published as US2017/0203092 on Jul. 20, 2017), both filed on Jan. 17, 2017 (the entire disclosures of both of which are incorporated herein by reference).

As these products are increasingly being used with pediatric patients, some conventional caps, with or without the disinfecting feature, on the market today can becomes lodged in the airway of a pediatric patient for example due to their relatively small size and ease of removal from a needleless connector. This kind of incident has been detailed in a recent study by the University of Cincinnati called "The Disinfection Cap as Esophageal Foreign Body," Tawfik et al. 2015.

An approach for addressing child safety by locking the cap to prevent a child's inadvertent removal of the cap from a needleless connector is described in a related U.S. patent application Ser. No. 15/957,208 (published as US2018/0304067 on Oct. 25, 2018) filed on Apr. 19, 2018 (the entire disclosures of which are incorporated herein by reference).

However, many current cap designs on the market today do not have any features that allow air to pass around the cap if the cap becomes lodged in an airway of a patient. If a cap is removed from, or is not attached to, a needleless connector, and becomes lodged in the throat of a patient, some such current cap designs can completely seal the windpipe and prevent a patient from breathing. That is, many designs of needleless connector caps on the market today may not allow air to easily flow through the windpipe, drastically decreasing the time that a nurse would have to remove the cap from the patient's throat.

Accordingly, child safety, and safety of a patient of any age, also needs to be addressed when a cap has been removed from, or is not attached to, a needleless connector.

SUMMARY

The matters exemplified in this description are provided to assist in a comprehensive understanding of exemplary embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

As would be readily appreciated by skilled artisans in the relevant art, while descriptive terms such as "lock", "hole", "tip", "hub", "thread", "sponge", "protrusion", "slope", "wall", "top", "side", "rib" and others are used throughout this specification to facilitate understanding, it is not intended to limit any components that can be used in combinations or individually to implement various aspects of the embodiments of the present invention.

Exemplary embodiments of the present invention provide needleless connector caps that can reduce the risk of having an airway blocked by a cap that may become lodged in an infant or child's (or any age patient) throat. In an exemplary implementation of the embodiments of present invention, a needleless connector cap includes one or more vent(s) allowing air to pass around the cap, even if the cap is completely concentric with a patient's throat.

According to exemplary implementations of the embodiments of the present invention, configuration of structural elements making up a cap exterior include one or more opening(s) in the cap that extend from the base to the top side of the cap forming one or more vent(s) allowing air to pass through the cap, even if the cap is completely concentric with the windpipe in a patient's throat. For example, external vents can be configured to encircle an exterior of the cap.

According to yet further exemplary implementations of the embodiments of the present invention, one or more opening(s) around an inner wall of the cap can be protected via an exterior wall, which can keep the opening(s) from contacting the windpipe and/or keep the opening(s) from becoming clogged and/or sealed by the surrounding tissue.

According to an exemplary implementations of the embodiments of the present invention, a cap comprises: an inner housing comprising; a first top wall; an essentially cylindrical first sidewall; and an open bottom formed by the first sidewall with an opening to an inner cavity within the inner housing for receiving a hub of a needleless connector. An outer housing comprises an essentially cylindrical second side wall configured to essentially surround said first sidewall. A support structure connects the first sidewall to the second sidewall forming an open space extending between the inner housing and the outer housing allowing air to pass between the outer housing and said the housing via said open space Optionally, according to exemplary implementations of any of the disclosed embodiments, configuration of structural elements making up the cap locking feature can be optimized or varied, for example inner housing, outer housing, and support structure can be integrally formed.

Optionally, according to further exemplary implementations of any of the disclosed embodiments, the support structure can comprise at least one protrusion between an outer surface of the first sidewall and an inner surface of the second sidewall.

Optionally, according to further exemplary implementations of any of the disclosed embodiments, at least one protrusion can comprise a first vertical surface essentially perpendicular to the outer surface of the first sidewall and the inner surface of the second sidewall. The protrusion can extend from the bottom formed by the first sidewall to the first top wall.

Optionally, according to further exemplary implementations of any of the disclosed embodiments, the cap can comprise a peel sealing film sealing the opening to the inner cavity when attached to a surface of a rim of the open bottom formed by the first sidewall.

Optionally, according to further exemplary implementations of any of the disclosed embodiments, the peel sealing film would not cover or block the open space extending between the inner housing and the outer housing.

Optionally, according to further exemplary implementations of any of the disclosed embodiments, cap can have an outer locking housing comprising a third top wall configured above the first top wall and comprising at least one opening extending through the third top wall allowing the air passing through the open space extending between the inner housing and the outer housing to pass through the outer locking housing, and an essentially cylindrical third side wall configured to essentially surround the second sidewall. The cap further having a safety interface comprising a first portion configured on an outer surface of the first top wall, and a second portion configured on an inner surface of the third top wall, wherein the safety interface transfers a rotational movement of the outer locking housing to a rotational movement of the inner housing and the outer housing in the same rotational direction when the first top wall and the third top wall are urged toward each other and the first portion and the second portion engage.

Optionally, according to further exemplary implementations of the disclosed embodiments with the safety interface, the first portion of the safety interface comprising at least one first protrusion, and the second portion of the safety interface comprises at least one second protrusion. Optionally, said first protrusion comprises a first vertical surface essentially perpendicular to said outer surface of said first top wall and a first slope surface at an acute angle to said outer surface of said first top wall, and the second protrusion comprises a second vertical surface essentially perpendicular to the inner surface of the second top wall and a second slope surface at an acute angle to the inner surface of the second top wall.

Optionally, according to further exemplary implementations of any of the disclosed embodiments, at least one of the outer housing and the inner housing comprises a first retaining feature, the outer locking housing comprises a third retaining feature, and the first retaining feature and the second retaining feature are configured to engage to secure the outer locking housing with respect to the inner housing and the outer housing and allow rotational movement of the outer locking housing with respect to the inner housing and the outer housing when the first portion of the safety interface and the second portion of the safety interface are not engaged. Optionally, the first retaining feature comprises a protrusion on an outer surface of the second sidewall of the outer housing, the second retaining feature comprises a recess in an inner surface of the third sidewall of the outer locking housing, the protrusion and the recess are configured to engage to secure the outer locking housing on the outer housing. Optionally, the first retaining feature comprises a first latching protrusion on an outer surface of the first top wall of said inner housing, the second retaining feature comprises a second latching protrusion on an inner surface of the third top wall of the outer locking housing, and the first latching protrusion and the second latching protrusion are configured to latch to secure the outer locking housing with respect to the inner housing and the outer housing.

Optionally, according to further exemplary implementations of any of the disclosed embodiments, a disinfection sponge configured within the inner cavity of the cap, and a removable cover seals the opening to the inner cavity to seal the sponge within the inner cavity prior to use of the cap.

Optionally, according to further exemplary implementations of any of the disclosed embodiments, the cap thread does not correspond to the mating feature of the needleless connector. Optionally, at least one of a major diameter, a minor diameter, a pitch, a thread section profile, and a number of threads of said cap thread does not correspond to said mating feature of said hub. Optionally, at least one cap thread on the inner sidewall surface of the sidewall comprises a protrusion formed on a least a portion of the cap thread to facilitate the interlocking with the mating feature of the needleless connector. Optionally, at least a portion of the at least one cap thread comprises a non-engaging portion that does not engage the mating feature of said needleless connector.

Optionally, according to further exemplary implementations of any of the disclosed embodiments, the cap includes a thread which has at least one interlocking portion formed on at least a portion of the cap thread to facilitate the interlocking with the mating feature of the needleless connector, and at least one non-engaging portions that does not engage the mating feature of the needleless connector.

Optionally, according to further exemplary implementations of any of the disclosed embodiments, the cap includes a thread which has a first start thread path, such that the first start thread path has a major profile, a minor profile, a pitch, and a first thread section profile, and at least a second start thread path, such that the second start thread path has a major profile, a minor profile, a pitch, and a second thread section profile, where the first thread section profile and the second thread section profile are different.

BRIEF DESCRIPTION OF THE DRAWINGS

Referring now to the drawings, wherein like reference numerals designate identical or corresponding parts throughout the several views, embodiments of the present invention are illustrated as follows.

DETAILED DESCRIPTION OF THE EXEMPLARY EMBODIMENTS

This matters exemplified in this description are provided to assist with a comprehensive understanding of exemplary embodiments with reference to the accompanying drawing figures. Accordingly, those of ordinary skill in the art will recognize that various changes and modifications of the exemplary embodiments described herein can be made within the scope of appended claims without departing from their full scope and equivalents. Also, descriptions of well-known functions and constructions are omitted for clarity and conciseness. Likewise, certain naming conventions, labels and terms as used in the context of the present disclosure are non-limiting and provided only for illustrative purposes to facilitate understanding of exemplary implementations of the exemplary embodiments.

As illustrated in FIGS. 3A-3D, respectively showing 3D view, isometric side view, cross sectional or side view, and top view, according to exemplary embodiments of the present invention a child safety cap 10 with a venting feature comprises an outer housing 20 including a sidewall 26, an inner housing 30 which includes a top wall 32 and a sidewall 36 with an opening 37 into inner cavity 38. Inner housing 30 is disposed within outer housing 20 such that sidewall 26 essentially surrounds sidewall 36, and top wall 32 remains essentially exposed. In an exemplary implementation of the embodiments of the present invention outer housing 20 can be connected to inner housing 30 by a support structure 40 forming open space 50 between outer housing 20 and inner housing 30 which allows air 1000 to pass around inner housing 30, between outer housing 20 and inner housing 30, or though the cap 10, even if the cap 10 is completely concentric with the windpipe in a patient's throat.

In an exemplary implementation, outer housing 20, inner housing 30 and support structure 40 can be integrally formed. FIGS. 3A-3D illustrate an exemplary implementation of support structure 40 comprising essentially linear protrusions or ribs 41 extending essentially from top 11 to base 12 of cap 10, and between outer surface 39 of inner sidewall 36 and inner surface 29 of outer sidewall 26, such that open space 50 comprises vents 51. However, other implementations of support structure 40 are within the scope of the embodiments of the present invention. Such other exemplary implementations of support structure 40 can take any number of shapes and forms as long as the resulting support structure 40 can keep the open space 50 from contacting the windpipe and/or keep the open space 50 from becoming clogged and/or sealed by the surrounding tissue. Non-limiting examples of other implementations of support structure 40 include plurality of non-linear ribs, or a single spiral thread-like rib, or a plurality of spacers of any shape, which may be disposed anywhere between, and connected to, outer surface 39 of sidewall 36 and inner surface 29 of outer sidewall 26. Such other support structures may also be integrally formed with at least one of side walls 36 and 26.

Figure 3A:
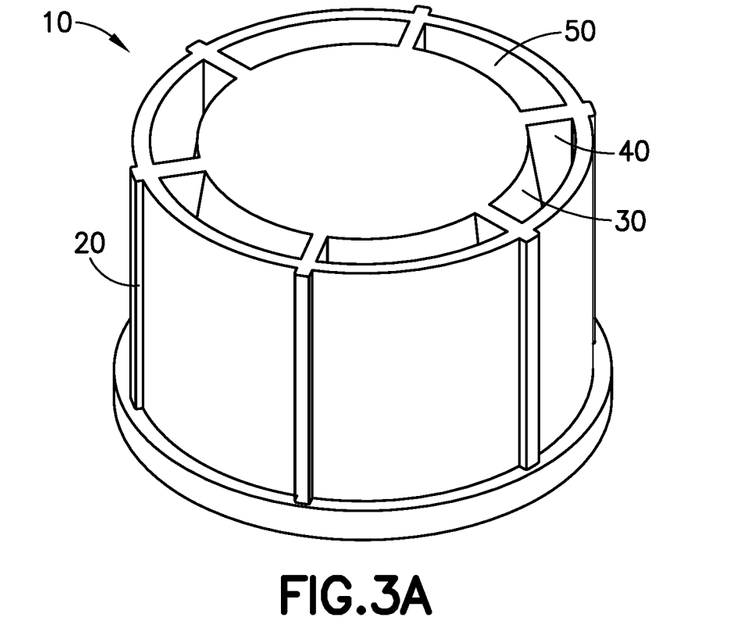
FIG. 3A is a three-dimensional views of a cap according to an exemplary embodiment of the present disclosure.
Figure 3B:
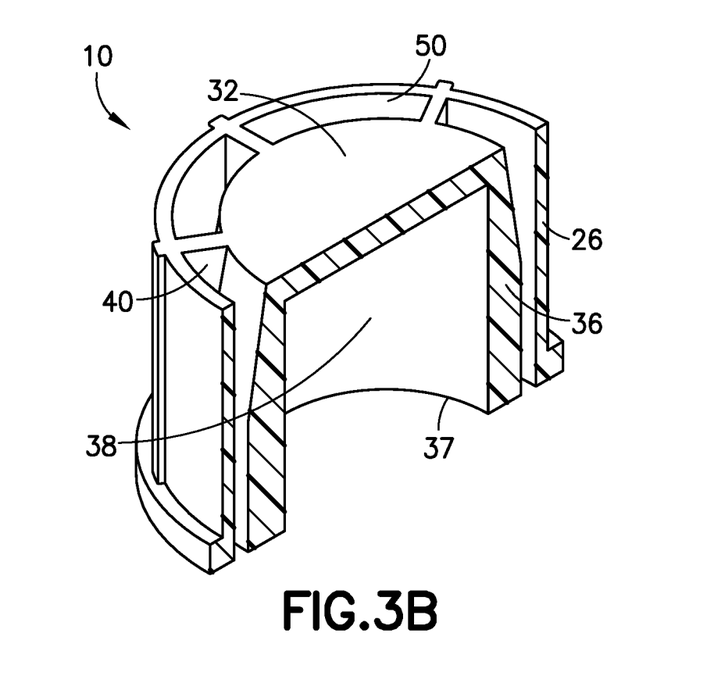
FIG. 3B is an isometric side view including a cross section of a cap according to an exemplary embodiment of the present disclosure.
Figure 3C:
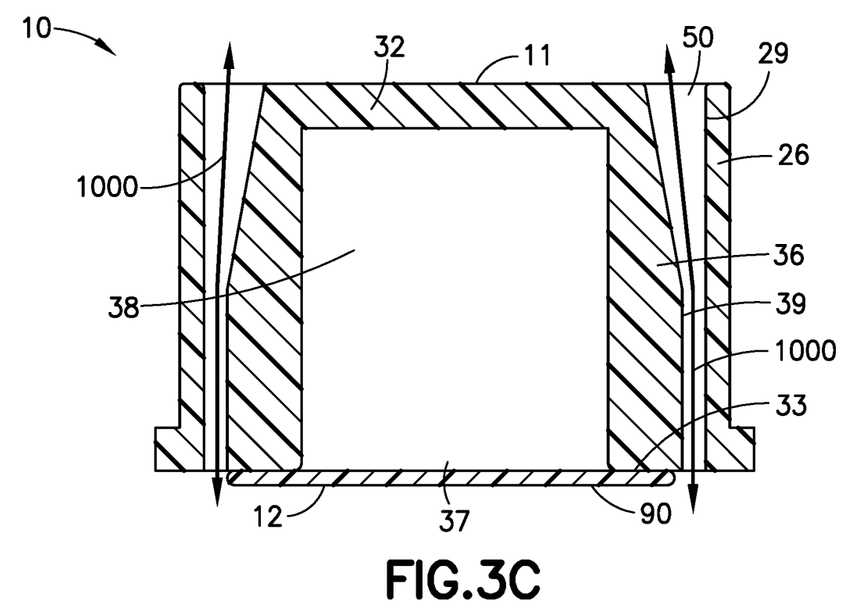
FIG. 3C is a cross sectional view of a cap according to an exemplary embodiment of the present disclosure.
Figure 3D:
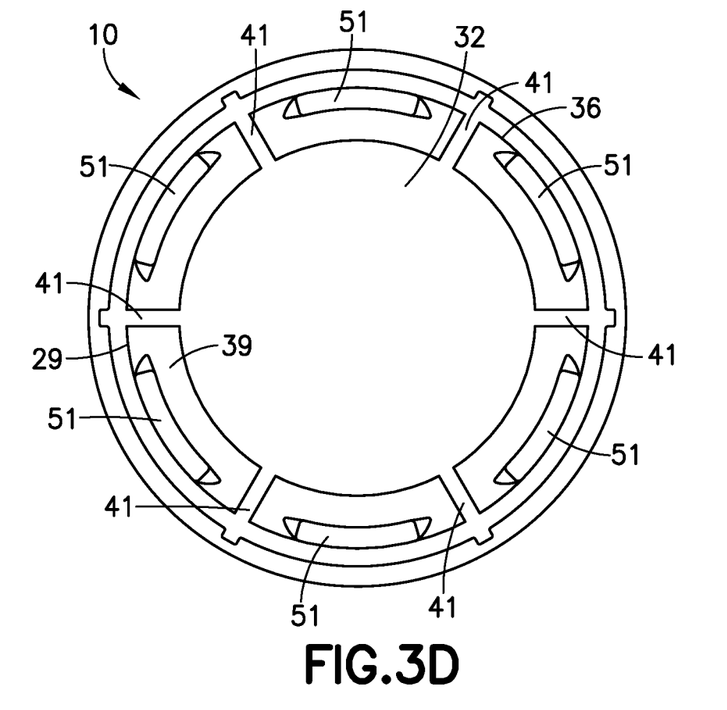
FIG. 3D is a top view of a cap according to an exemplary embodiment of the present disclosure

As further illustrated in FIG. 3C, according to exemplary embodiments of the present invention a peel sealing film 90 seals opening 37 when attached to a sealing surface, which can be constituted by a surface 33 of a rim of an open bottom of sidewall 36. In an exemplary implementation, peel sealing film 90 does not cover or block open space 50, for example by not extending beyond the rim of sidewall 36, such that open space 50 between outer housing 20 an inner housing 30 allows air to pass around inner housing 30, between outer housing 20 and inner housing 30, or though the cap 10, even if the cap 10 still has peel sealing film 90 attached thereto when it is completely concentric with the windpipe in a patient's throat.

Figure 4A:
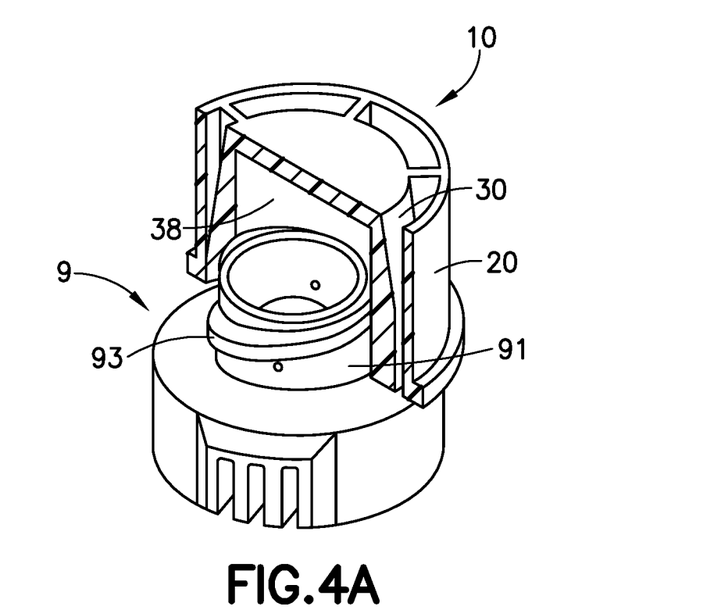
FIG. 4A is a three-dimensional side views of a cap according to yet another exemplary embodiment of the present disclosure disposed on a medical implement such as a needleless connector.
Figure 4B:
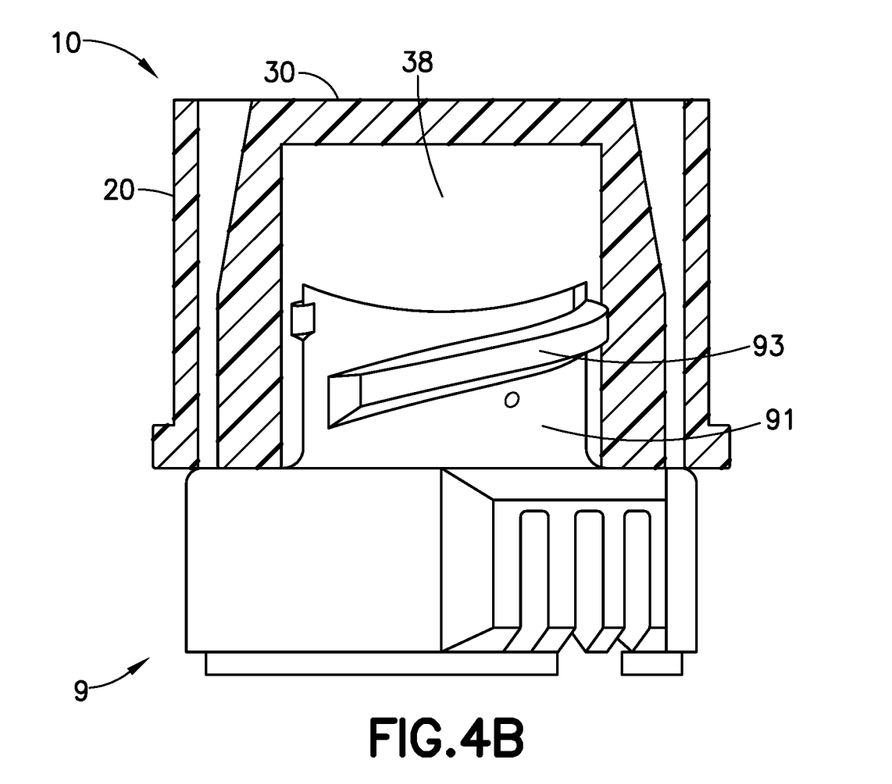
FIG. 4B is an illustration showing a cross-sectional view of a cap according to an exemplary embodiment of the present disclosure on a medical implement such as a needleless connector.

As illustrated in the examples of FIGS. 4A and 4B, respectively showing side view and isometric side view of cap 10 when attached to a connector 9, cavity 38 of inner housing 30 receives a tip 91 of a needleless connector 9 and secures the tip of needleless connector 9 within cavity 38, for example by having a thread feature within cavity 38 (see, for example, FIGS. 1 and 2, as well as FIGS. 6A, 6B, and 7 described in more detail below) that interlocks with a mating feature 93 (such as thread or a protrusion) of a hub or tip 91 of needleless connector 9, as described for example in related U.S. patent application Ser. Nos. 15/408,278 and 15/408,187, both filed on Jan. 17, 2017.

Figure 5A:
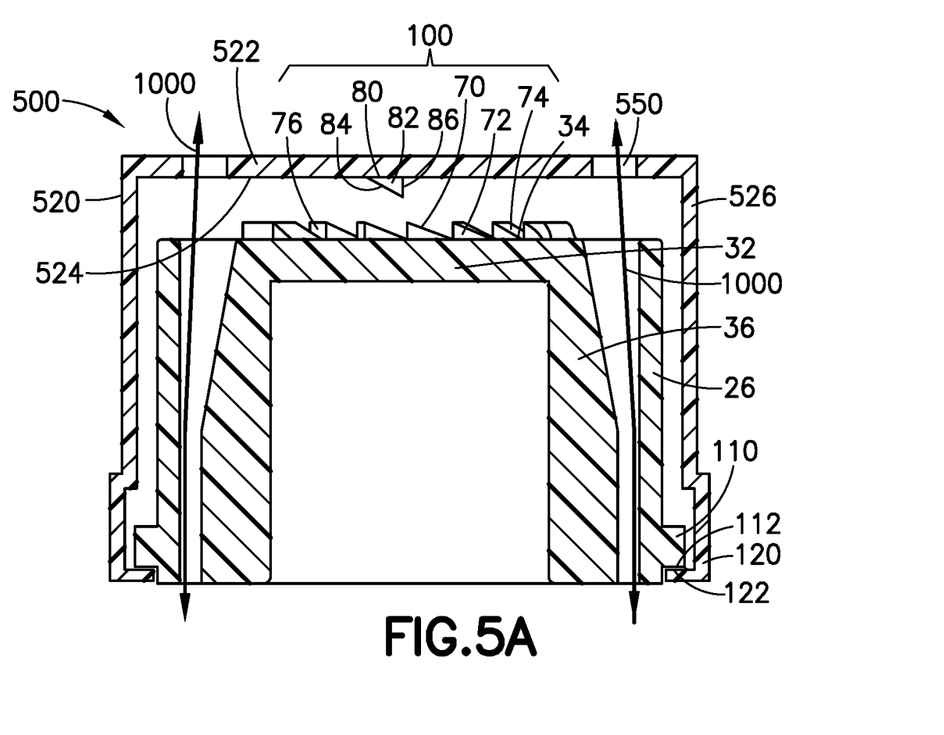
FIGS. 5A and 5B are illustrations showing a cross-sectional view and a top view, respectively, of a cap according to yet another exemplary implementation of embodiments of the present disclosure.
Figure 5B:
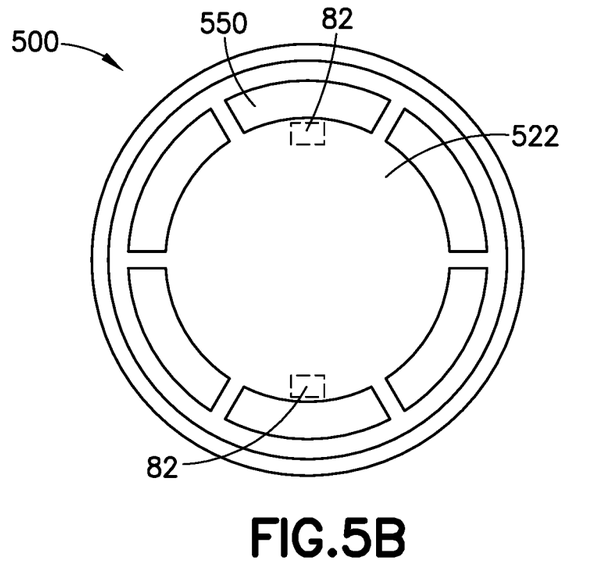

Referring to FIGS. 5A and 5B, respectively showing a section view and a top view, in exemplary implementations of the embodiments of the present invention, cap 500 can include a locking feature, as described for example in related U.S. patent application Ser. No. 15/957,208 filed on Apr. 19, 2018 and published as US2018/0304067 on Oct. 25, 2018, in conjunction with a venting feature of cap 10. For example, cap 500 comprises an outer locking housing 520 including a sidewall 526 and a top wall 522 such that sidewall 526 essentially surrounds sidewall 26, and top wall 522 essentially covers top wall 32. A safety interface 100 comprises a first portion 70 that can be configured on an outer surface 34 of top wall 32 of inner housing 30 as a ratchet feature comprising one or more protrusions 72 such as a tooth or teeth having a first slope surface 74 and a first vertical surface 76, and a second portion 80 that can be configured on an inner surface 524 of top 522 of outer locking housing 520 as a ratchet feature comprising one or more protrusions 82 such as a tooth or teeth having a second slope surface 84 and a second vertical surface 86. The first vertical surface 76 can be essentially perpendicular to the outer surface 34, and the first slope surface 74 can be at an acute angle to the outer surface 34. On the other hand, the second vertical surface 86 can be essentially perpendicular to the inner surface 524, and the second slope surface 84 can be at an acute angle to the inner surface 524.

Safety interface 100 is configured such that first portion 70 and second portion 80 do not engage unless the outer surface 34 is sufficiently near the inner surface 524 such that protrusions 72 and 82 can make sufficient contact.

According to a further exemplary implementation of the embodiments of the present invention as illustrated in detail in the example of FIG. 5A, a retaining interface to secure outer locking housing 520 with respect to outer sidewall 26 can be implemented for example as follows. An outer surface 29 of outer sidewall 26 can include an outer locking housing retaining feature such as a protrusion (or a skirt, or a flange) 110, and an inner surface of sidewall 526 of outer locking housing 520 can include an outer locking housing retaining feature such as a recess 120. Protrusion 110 and recess 120 are configured to engage, for example at respective first contact surface 112 of protrusion 110 and second contact surface 122 of recess 120, such that outer locking housing 520 is secured on outer sidewall 26 while allowing rotational movement of outer locking hosing 520 with respect to outer sidewall 26, as illustrated for example in FIGS. 5 and 6 of U.S. Provisional Patent Application No. 62/488,266 filed on Apr. 21, 2017.

A retaining interface secures outer locking housing 520 with respect to outer sidewall 26 and top wall 32 while allowing sufficient axial movement of the outer surface 34 with respect to the inner surface 524 such that on the one hand protrusions 72 and 82 do not necessarily contact each other when outer locking housing 520 is rotated with respect to outer sidewall 26 and top wall 32, and on the other hand protrusions 72 and 82 make sufficient contact with each other to transfer rotational movement of outer locking housing 520 to inner housing 30 and outer housing 20.

As further illustrated in FIG. 5B by a top view of outer locking housing 520, top wall 522 includes opening(s) 550 allowing air to pass through outer locking housing 520. While FIG. 5B illustrates six opening that essentially correspond to vents 51 of open space 50 (see FIG. 3D), any number or shape of opening(s) 550 are within the scope of the embodiments of the present invention so long as the opening(s) 550 not interfere with structural integrity and function of the locking feature, and opening(s) 550 in conjunctions with open space 50 allow air to pass around inner sidewall 36, between outer sidewall 26 and inner sidewall 36, though top wall 522, or though the cap 500, even if cap 500 is completely concentric with the windpipe in a patient's throat.

According to exemplary implementations of the embodiments of the present invention, housing of cap 10 having the safety features described above with reference to FIGS. 3A-3D can be implemented with all of the disinfectant caps having various features and designs described in Applicant's co-pending US patent applications Nos. U.S. patent application Ser. No. 15/408,278 and U.S. patent application Ser. No. 15/408,187, both filed on Jan. 17, 2017, by modifying the housings of the disinfectant caps disclosed therein as shown in an illustrative example of FIGS. 6A and 6B.

Figure 6A:
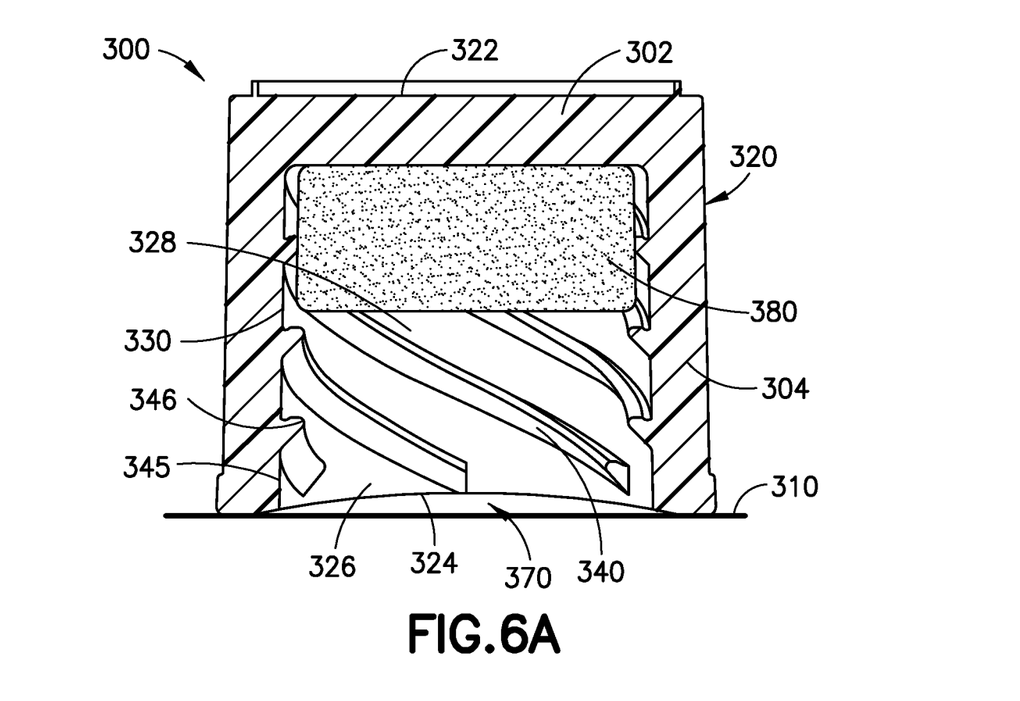
FIG. 6A is a cross-sectional view of a cap according to yet another exemplary implementation of embodiments of the present disclosure.
Figure 6B:
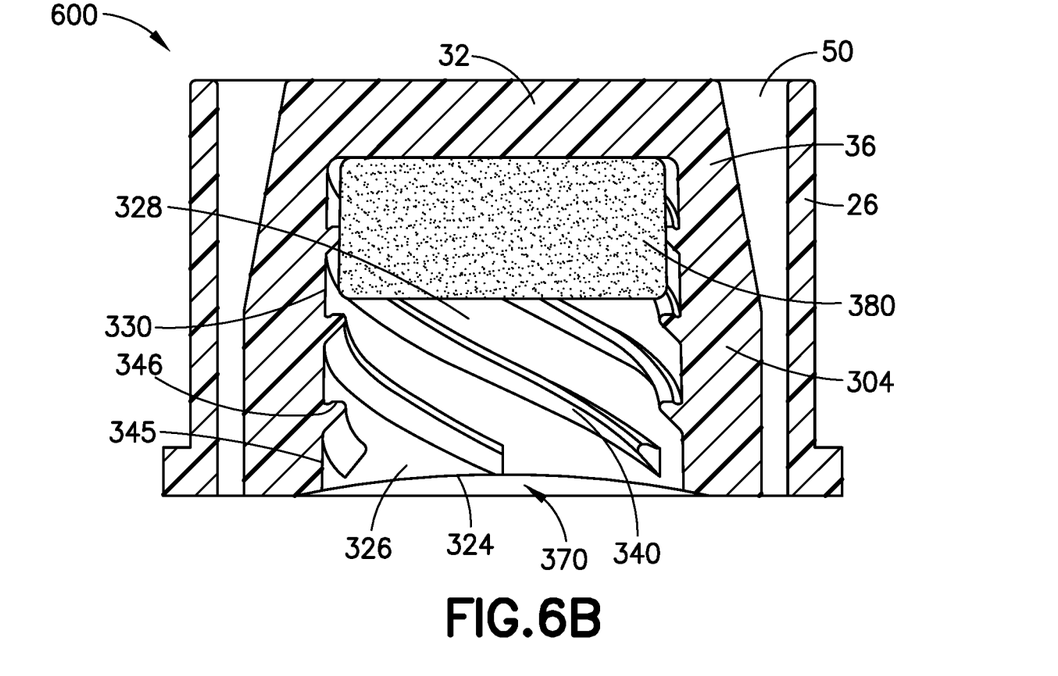
FIG. 6B is a cross-sectional view of a cap according to yet another exemplary implementation of embodiments of the present disclosure.

Referring to FIG. 6A, a cross thread disinfecting cap 300 has housing 302 comprising: a closed top 322; an essentially cylindrical sidewall 304 with an outer sidewall surface 320; and an open bottom 324 with an opening 326 to an inner cavity 328 within housing 302 for receiving tip of a needleless connector. The bottom 324 formed by sidewall 304 of housing 302 is not flat such that space 370 exists between a flat surface 310 and bottom 324 of cap 300. The inner cavity 328 can accommodate an alcohol soaked disinfection sponge 380 and has threads 340 on inner sidewall surface 330 of sidewall 304. The diameter (major diameter 345 and/or minor diameter 346) of threads 340 of the cap 300 may not correspond to the thread of a needleless connector.

Referring to FIG. 7B, cap 600 according to exemplary embodiments of the present invention includes all of the features of cap 300, but with sidewall 304 of housing 302 modified as illustrated in the examples of FIGS. 3A-3D to include: inner sidewall 36 with a top wall 32; outer sidewall 26 essentially surrounding sidewall 36 such that top wall 32 remains essentially exposed; support structure 40 (see FIGS. 3A and 3B) forming open space 50 between outer sidewall 26 and inner sidewall 36 allowing air to pass around inner sidewall 36, between outer sidewall 26 and inner sidewall 36, or though the cap 600, even if the cap 600 is completely concentric with the windpipe in a patient's throat.

According to further exemplary implementations of the embodiments of the present invention, housing of cap 500 having the safety features described above with reference to FIGS. 3A-3D, 5A, and 5B including venting feature described herein and any locking feature, as described for example in Applicant's related U.S. Provisional Patent Application No. 62/488,266 filed on Apr. 21, 2017, can be implemented in all of the disinfectant caps having various features and designs described in Applicant's co-pending US patent applications Nos. U.S. patent application Ser. Nos. 15/408,278 and 15/408,187, both filed on Jan. 17, 2017, by further modifying the housings of the disinfectant caps disclosed therein as shown in an illustrative example of FIG. 7.

Figure 7:
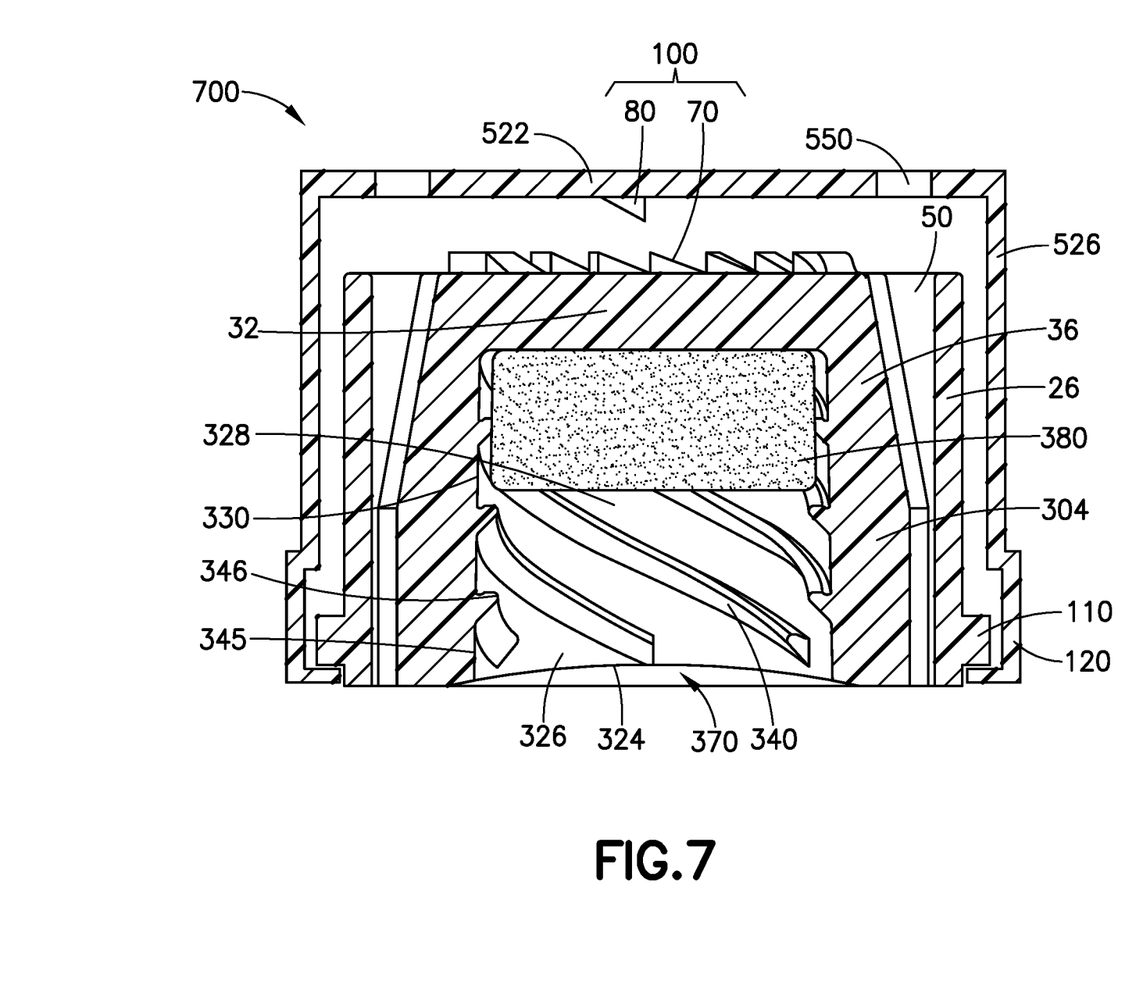
FIG. 7 is a cross-sectional view of a cap according to yet another exemplary implementation of embodiments of the present disclosure

Referring to FIG. 7, cap 700 according to exemplary embodiments of the present invention includes all of the features of cap 600 further modified as illustrated in the examples of FIGS. 5A and 5B to include: outer locking housing 520; a safety interface 100 comprising a first portion 70 configured on outer surface of top wall 32 and a second portion 80 configured on an inner surface of top wall 522; and a retaining interface to secure outer locking housing 520 with respect to outer sidewall 26 implemented by cooperating protrusion 110 and recess 120 as described above with reference to FIG. 6B. Outer locking housing 520 includes opening(s) 550 in its top wall 522 which cooperate with open space 50 between outer sidewall 26 and inner sidewall 36 allowing air to pass around inner sidewall 36, between outer sidewall 26 and inner sidewall 36, through opening(s) 550, or though the cap 700, even if the cap 700 is completely concentric with the windpipe in a patient's throat.

While the present invention has been shown and described with reference to certain exemplary embodiments thereof, it will be understood by those skilled in the art that various changes in form and details may be made therein without departing from the spirit and scope of the embodiments of the present invention. For example, a disinfection sponge can comprise any suitable disinfecting or other application-specific substance, and can be made of any suitable material. Also, the housing and/or the outer locking housing of the cap can be single shot molded, or made by other suitable process. Furthermore, any of the features or elements of any exemplary implementations of the embodiments of the present invention as describes above and illustrated in the drawing figures can be implemented individually or in any combination(s) as would be readily appreciated by skilled artisans without departing from the spirit and scope of the embodiments of the present invention.

In addition, the included drawing figures further describe non-limiting examples of implementations of certain exemplary embodiments of the present invention and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the invention will become apparent to those skilled in the art from the details provided, which, taken in conjunction with the annexed drawing figures, disclose exemplary embodiments of the invention.

I claim:

1. A cap comprising:
an inner housing comprising
a first top wall,
an essentially cylindrical first sidewall, and
an open bottom formed by said first sidewall with an opening to an inner cavity within said inner housing for receiving a hub of a needleless connector;
an outer housing comprising an essentially cylindrical second side wall configured to essentially surround said first sidewall;
wherein said first sidewall is connected to said second sidewall forming an open space that extends between said inner housing and said outer housing allowing air to pass between said outer housing and said inner housing via said open space;
an outer locking housing comprising
a third top wall configured above said first top wall and comprising at least one opening extending through said third top wall allowing said air passing through said open space extending between said inner housing and said outer housing to pass through said outer locking housing, and
an essentially cylindrical third sidewall configured to essentially surround said second sidewall;
wherein said outer locking housing interfaces with said outer housing whereby a rotational movement of said outer locking housing is transferred to a rotational movement of said inner housing and said outer housing in the same rotational direction when said first top wall and said third top wall are urged toward each other and a first portion of an outer surface of said first top wall and a second portion of an inner surface of said third top wall engage.

2. The cap of claim 1, wherein said inner housing and said outer housing are integrally formed.

3. The cap of claim 1 further comprising at least one protrusion between an outer surface of said first sidewall and an inner surface of said second sidewall, said at least one protrusion connecting said first sidewall to said second sidewall to form said open space.

4. The cap of claim 3 wherein: said at least one protrusion comprises a first vertical surface essentially perpendicular to said outer surface of said first sidewall and said inner surface of said second sidewall, and said at least one protrusion extends from said open bottom formed by said first sidewall to said first top wall.

5. The cap of claim 1 further comprising a peel sealing film sealing said opening to said inner cavity when attached to a surface of a rim of said open bottom formed by said first sidewall.

6. The cap of claim 5 wherein said peel sealing film does not cover or block said open space extending between said inner housing and said outer housing.

7. The cap of claim 1 wherein:
said first portion of said outer surface of said first top wall comprises at least one first protrusion, and
said second portion of said inner surface of said third top wall comprises at least one second protrusion.

8. The cap of claim 7, wherein
said at least one first protrusion comprises a first vertical surface essentially perpendicular to said outer surface of said first top wall and a first slope surface at an acute angle to said outer surface of said first top wall, and
said at least one second protrusion comprises a second vertical surface essentially perpendicular to said inner surface of said third top wall and a second slope surface at an acute angle to said inner surface of said third top wall.

9. The cap of claim 1 wherein: when said first portion and said second portion are engaged, said outer locking housing is secured with respect to said inner housing and said outer housing while allowing rotational movement of said outer locking housing with respect to said inner housing and said outer housing when said first portion and said second portion are not engaged.

10. The cap of claim 9 further comprising:
a protrusion on an outer surface of said second sidewall of said outer housing; and
a recess in an inner surface of said third sidewall of said outer locking housing, wherein
said protrusion and said recess are configured to engage to secure said outer locking housing on said outer housing.

11. The cap of claim 9 further comprising:
a first latching protrusion on said outer surface of said first top wall of said inner housing; and
a second latching protrusion on said inner surface of said third top wall of said outer locking housing, wherein
said first latching protrusion and said second latching protrusion are configured to latch to secure said outer locking housing with respect to said inner housing and said outer housing.

* * * * *